United States Patent [19]
Smith et al.

[11] Patent Number: 5,522,264
[45] Date of Patent: Jun. 4, 1996

[54] METHOD AND APPARATUS FOR DETECTING AND MEASURING GELLED PIGS IN TUBULARS

[75] Inventors: Lonnie J. Smith, Parker; Keith W. Katahara, Allen, both of Tex.

[73] Assignee: Atlantic Richfield Company, Los Angeles, Calif.

[21] Appl. No.: 194,972

[22] Filed: Feb. 14, 1994

[51] Int. Cl.⁶ .................................................. G01N 29/18
[52] U.S. Cl. ........................ 73/610; 73/432.1; 73/DIG. 1
[58] Field of Search ............................. 73/597, 598, 609, 73/610, 661, 290 V, 865.5, 432.1, DIG. 1, 40.5 R, 54.41, 64.42, 64.53

[56] References Cited

U.S. PATENT DOCUMENTS

| | | |
|---|---|---|
| 5,215,781 | 6/1993 | Lowther . |
| 5,343,737 | 9/1994 | Baumoel ............................. 73/40.5 R |
| 5,417,112 | 5/1995 | Rosenberg .................... 73/587 |

FOREIGN PATENT DOCUMENTS 957910  11/1974  Canada .

OTHER PUBLICATIONS

"The Use of Gelly Pig Technology for Removal of Stuck Mechanical Pigs" by D. P. Nesbitt, OTC 6772, Houston, Texas May 6–9, 1991.

*Primary Examiner*—Hezron E. Williams
*Assistant Examiner*—Rose M. Finley
*Attorney, Agent, or Firm*—Drude Faulconer

[57] ABSTRACT

A method and apparatus for detecting and measuring gelled material (i.e. gelled pig) as it passes through a tubular by generating ultrasonic pulses at timed intervals which, in turn, are transmitted through said tubular and materials flowing therethrough at a fixed point along said tubular. These pulses are received after they have passed through said tubular and the materials and are processed to identify those pulses which travel through said gelled material as said gelled material passes by said fixed point. From the number of identified pulses, the length of the gelled pig can be determined.

9 Claims, 3 Drawing Sheets

METHOD AND APPARATUS FOR DETECTING AND MEASURING GELLED PIGS IN TUBULARS

DESCRIPTION

1. Technical Field

The present invention relates to a method and apparatus for detecting and measuring a gelled pig in tubulars and in one of its aspects relates to a method and apparatus for detecting and measuring the length of a gelled pig at a fixed point along in a pipeline by using ultrasonic pulses.

2. Background Art

Most tubulars which carry fluids must be treated periodically to extend their operational life and/or to improve and maintain their operating efficiencies. For example, well tubing and casing strings, pipelines, and the like used for transporting crude oil and/or natural gas which contain even small amounts of water routinely experience severe corrosion problems which, if not timely treated, can result in early failure of the line. Also, the interior surfaces of such tubulars have a substantial "roughness" even when new which increases with scaling, pitting, etc. during use. As this roughness increases, the friction or "drag" between the tubular wall and the fluids flowing therethrough increases thereby substantially reducing the flowrate through the tubular. Further, debris, e.g. rust flakes, etc. , may collect in the line which can seriously affect the overall efficiency of the pipeline.

"Gelled pigs" are now routinely used in treating tubulars. For example, gelled pigs formed of different gelled materials have been used to deposit corrosion inhibitors and/or drag reducers to the interior walls of pipelines; see Canadian Patent No. 957,910 and U.S. Pat. No. 5,215,781. Further, gelled pigs have been proposed as an interface control for different fluids flowing in the same pipeline while removing residual fluids (e.g. water) and/or solids from the pipeline: see U.S. Pat. No. 4,003,393.

A "gelled pig", as used herein, is a compliant mass of a gelled material which substantially conforms to the interior of the tubular as it is forced therethrough by the fluids normally flowing through the tubular. The gelled material, itself, may range from sophisticated, gelled hydrocarbons (e.g. Canadian Patent No. 957,910 and U.S. Pat. No. 4,003, 393) to common gelatin (see U.S. Pat. No. 5,215,781). Gelled pigs have several advantages over rigid or mechanical pigs. For example, gelled pigs resiliently deform to (1) pass through tubulars of differing diameters; (2) pass through line restrictions such as chokes; and (3) expand radially as they are pumped through the tubular thereby remaining in contact with the wall of the pipe over long distances.

In order to assess the distribution of treatment chemicals (e.g. corrosion inhibitor, drag reducer, etc.) and/or the overall effectiveness of a particular gelled pig and the operation being carried out, it is desirable to detect and measure the length of a pig as it passes a fixed point (i.e. a particular location) along the pipeline. Also, where a slug of chemical is "sandwiched" and carried between two spaced gelled pigs, it is desirable to be able to measure the amount of chemical left between the two pigs as they pass that location.

Unfortunately, due to the soft consistency of a gelled pig, the conventional mechanical devices sometimes used to detect other type of pigs in a tubular are unable to detect and/or measure the length of a gel led pig. Accordingly, a need exists for accurately detecting and measuring a gelled pig in a tubular as it travels therethrough.

SUMMARY OF THE INVENTION

The present invention provides a method and apparatus for detecting and measuring gelled material (i.e. gelled pig ) as it passes through a tubular by generating ultrasonic pulses at timed intervals at a fixed point along the tubular which, in turn, are transmitted through said tubular and the materials flowing therethrough at that point. These pulses are received on the opposite side of the tubular and are processed to identify and record only those pulses which travel through said gelled material as said gelled material passes by said fixed point.

More specifically, the present invention utilizes an apparatus comprised of a first or an ultrasonic pulse transmitting transducer and a second or an ultrasonic pulse receiving transducer which are mounted diametrically-opposed to each other onto the exterior of a tubular at a fixed point. The transmitting transducer is connected to a clock-driven, pulse generator or pulser which, in turn, generates ultrasonic pulses at a set frequency or timed interval (e.g. about 50 Hz to about 1000 Hz) depending on a particular tubular-treating application. The first transducer transmits each pulse through the abutting wall of the tubular, through any material flowing within tubular, and through the opposing wall where each pulse is received by the second transducer.

Due to the differences in the ultasonic properties of the pipeline fluids and the gelled material (i.e. gelled pig), the velocity of each pulse (e.g. 4.8 km/sec.) in the pipeline fluids (e.g. oil, water) is slower than the pulse velocity (e.g. 6.3 km/sec.) through the gelled material (e.g. gelatin). Accordingly, each pulse through the gelled material has a shorter travel time after transmission and each arrives at the second transducer earlier than the slower pulses which travel through the other materials in the pipeline (e.g. fluids).

The apparatus includes a gate which is synchronized and set to open and remain open only long enough to detect the high velocity pulses (i.e. those travelling through the gelled material) and to close before the arrival of a slower pulse (i.e. those travelling through water or oil). In other words, a pulse through the gelled material will arrive at the gate while it is open and will pass through the gate to be counted by a counter. The actual length of the gel led material (i.e. a pig) can then be calculated by multiplying the time (i.e. time represented by the number of gated clock pulses as recorded by the counter ) by the known flowrate within the tubular.

In some tubular treatment operations, it may be desirable to measure the length of a slug of treating chemical (e.g. corrosion inhibitor and/or drag reducer) as it is carried through a tubular sandwiched between two spaced gelled pigs. To measure the length of such a slug, the gated pulses from the second transducer are fed to pulse stretcher to produce two long or "stretched" pulses (i.e. representively of the lengths of the two spaced plugs) having an interval therebetween during which no gated pulses are recorded. The time of this interval between the pigs is then multiplied by the flowrate of the fluids in tubular to calculate the length, hence the volume, of the slug.

BRIEF DESCRIPTION OF THE DRAWINGS

The actual construction, operation, and apparent advantages of the present invention will be better understood by referring to the drawings in which like numerals refer to like parts and in which.

BEST KNOWN MODE FOR CARRYING OUT INVENTION

Figure 1:
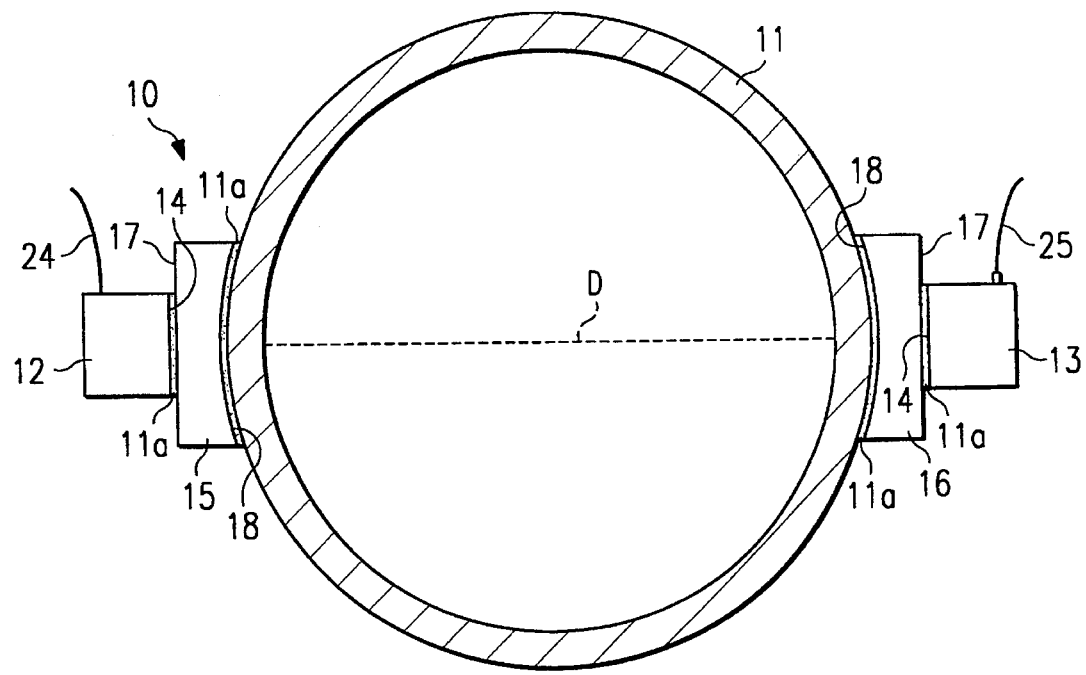
FIG. 1 is a cross-sectional view of one embodiment of an apparatus in accordance with the present invention for detecting and measuring a gelled pig in a tubular which is mounted on said tubular.

Referring more particularly to the drawings, FIG. 1 discloses an apparatus 10 for detecting and measuring the length of a gelled pig (not shown) as the pig passes through tubular 11. Basically, apparatus 10 is comprised of an ultrasonic pulse transmitting transducer 12 and an ultrasonic pulse receiving transducer 13 which, in turn, are mounted diametrically-opposed to each other onto the exterior of tubular 11. Transducers 12, 13 may be selected from several inexpensive, off-the-shelf, commercially-available NDT tranducers (e.g. transducers available from Etalon, Inc., Lizton, Ind.) with the actual size and frequency ranges being determined by the particular application in which they are to be used. For example, for a relatively large tubular (e.g. 24-inch diameter steel pipe), a 1-inch diameter, 0.5 MHz transducer is preferred while smaller diameter tubulars will generally require smaller diameter, higher frequency transducers.

Since most off-the-shelf tranducers have a flat, front face 14, mounting blocks 15, 16, each having a flat surface 17 on one side and a curvature 18 which matches the curvature of tubular 11 on the side, are used to mount transducers 12, 13, respectively, into contact with exterior wall of tubular 11. Blocks 15, 16 are made of a material, e.g. steel, which has similar acoustic properties to those of the tubular 11 so that the ultrasonic pulses are not unnecessarily refracted or distorted as they pass through the adapters and the wall of the tubular thereby substantially simplifying the processing of the received pulses. Further, to ensure good ascoutical coupling between the transducers, blocks, and the tubular 11, a layer of grease 11a or similar material may be used between the interfaces of the various elements as illustrated in FIG. 1.

Figure 2:
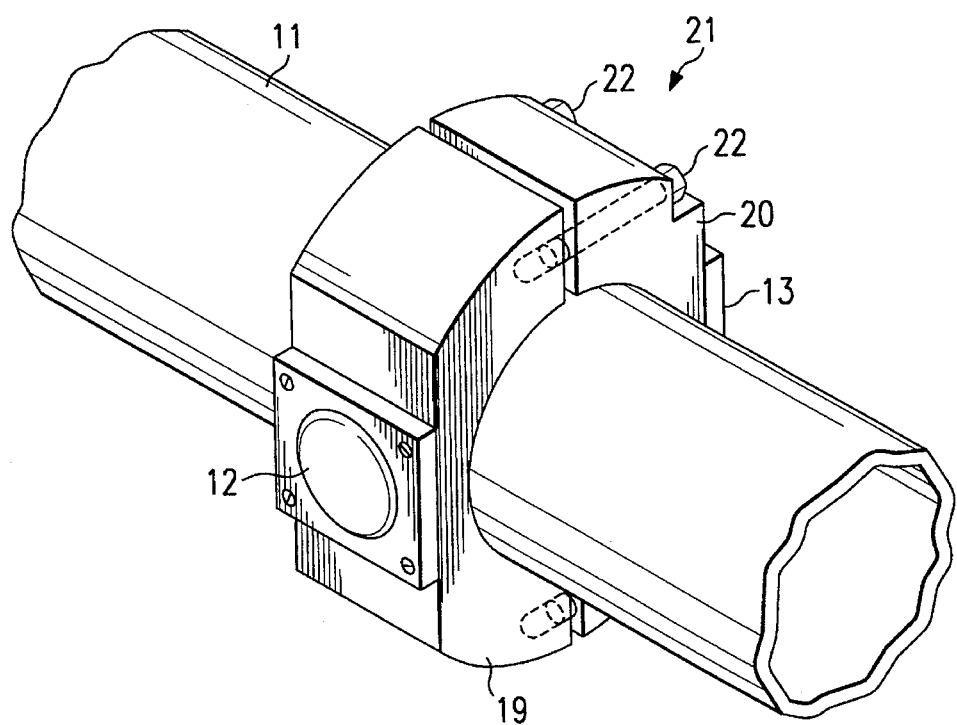
FIG. 2 is a perspective view of an actual means for mounting the transducers of FIG. 1 onto a tubular.

FIG. 2 discloses one means for mounting the transducers onto tubular 11 wherein tranducers 12, 13 are mounted into segments 19, 20, respectively, of collar 21 or the like, which, in turn, are secured onto tubular 11 by bolts 22 (only one shown) or the like. Further, while transducers 12, 13 are illustrated as being mounted diametrically-opposed across the horizontal diameter of tubular 11, it should be understood that the transducers can also be mounted diametrically-opposed across other diameters of tubular 11 (e.g. vertical diameter) without departing from the present invention.

Figure 3:
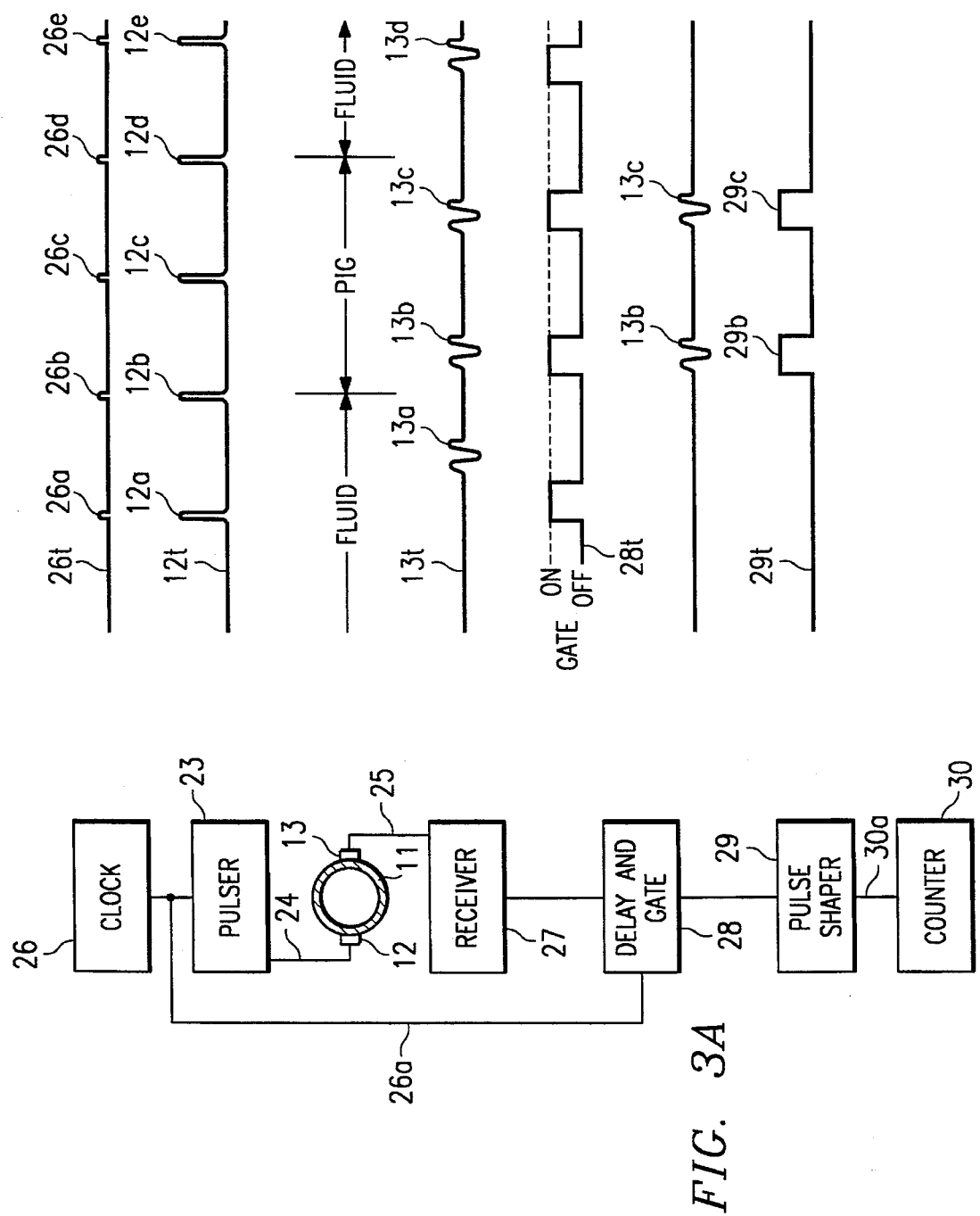
FIG. 3A is a schematical flow diagram of the apparatus of the present invention.
FIG. 3B is an idealized representation of the respective time function curves generated by the apparatus of FIG. 3A.

FIG. 3A discloses the circuity and components associated with apparatus 10 for generating, receiving, and processing the ultrasonic pulses in detecting and/measuring a gelled pig as it moves through tubular 11 past apparatus 10 and FIG. 3B discloses the time function curves which are generated by the respective components of FIG. 3A. Transmitting transducer 12 is coupled through lead 24 to an ultrasonic pulse generator or pulser 23 ( e.g. Model 5055 PR, Panametrics, Waltham, Mass.) which is driven by a clock 26 which, in turn, pulses at a frequency or timed intervals (i.e. 26a–26e on time curve 26t) which may range from about 50 Hz to about 1000 Hz depending on a particular application (i.e. tubular size, the flowrate through the tubular, size of pig, etc.). It should be understood that the actual flowrate, size of pig(s), densities of the pipeline fluids and gelled material, etc. all will be known for a particular pipeline treating operation.

Pulser 23 applies a high voltage, electrical pulse (12a–12e on time curve 12t) to transmitting transducer 12 at each clock pulse. Transducer 12, in turn, transmits ultrasonic pulses through the abutting wall of the tubular 11, through material within tubular, and through the opposing tubular wall where each pulse (i.e. 13a–13d on time curve 13t) is received by receiving transducer 13. Due to the differences in the densities of the pipeline fluids and the gelled material (i.e. gelled pig), the velocity of each pulse (e.g. 4.8 km/sec.) in the pipeline fluids (e.g. oil, water) is slower than that (e.g. 6.3 km/sec.) through gelled material (e.g. gelatin). This contrast in velocities has been experimentally found to continue even under high temperatures in the tubular. Accordingly, the pulses (i.e. 12b, 12c on time curve 12t) which travel through the gelled material arrive at transducer 13 earlier (i.e. 13b, 13c on time curve 13t) than the pulses (i.e. 12a, 12d, 12e) which travel through the pipeline fluids (i.e. 13a, 13d).

Receiver transducer 13 is connected by lead 25 to receiver 27 which amplifies the received pulses. The amplified pulses then go to gate 28 which is synchronized with clock 26 through line 26a and is set to open and remain open only long enough to detect the high velocity pulses (i.e. those travelling through the gelled material) while the gate will close before the arrival of the slower pulses (i.e. those travelling through water or oil). Gate 28 may also contains circuits for external triggering and for adjusting delay and gate width times (e.g. Model 5052 G, Panametrics).

When gate 28 is open as seen on time curve 28, pulses 13b and 13c pass through the gate into detector or pulse shaper 29 which, in turn, puts out a single pulse (i.e. 29b, 29c on time curve 29t) for each gated pulse arrival. Each gated pulse passes through lead 30a to counter 30 which measures the time it takes a gelled pig to pass by the opposed transducers of apparatus 10 (i.e. two clock pulses as represented by gated pulses 29b, 29c) in the drawings. The actual pig length can then be calculated by multiplying the time (i.e. time represented by the gated clock pulses) by the known flowrate within tubular 11.

Figure 4:
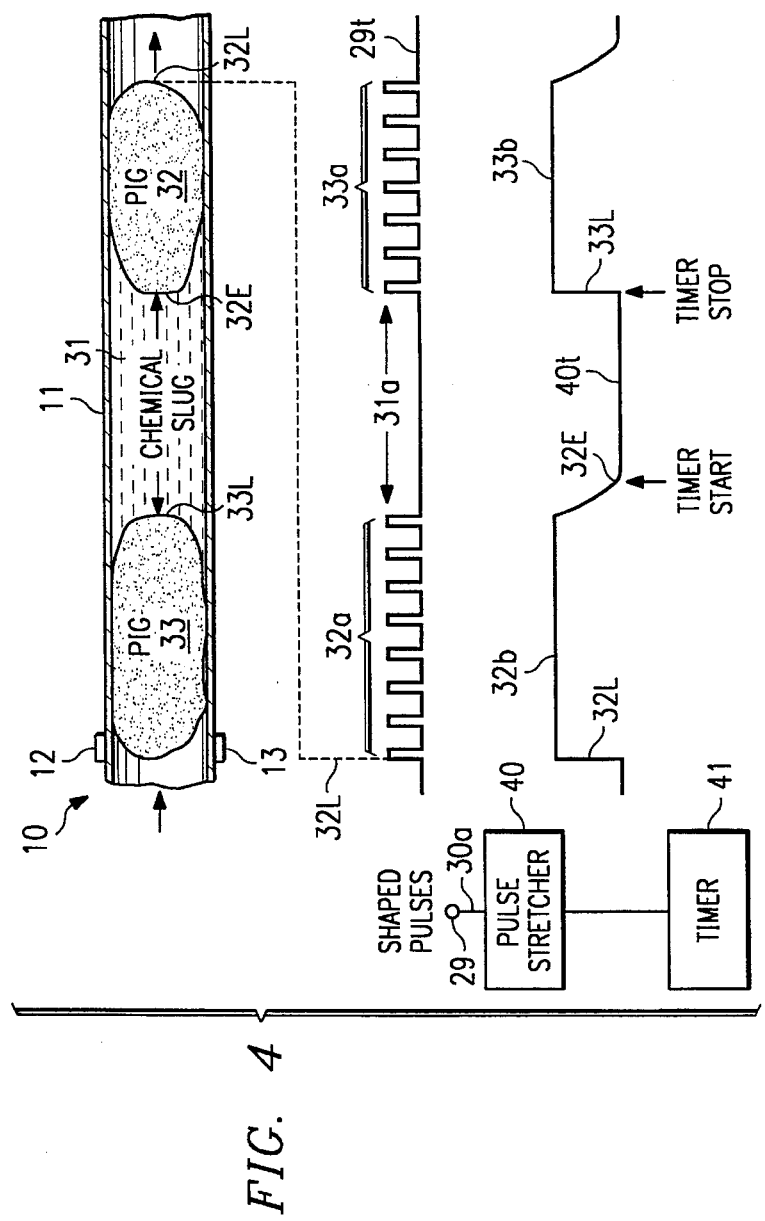
FIG. 4 is a schematical flow diagram of additional components which may be added to those of FIG. 3 for measuring the length of a chemical slug between two spaced gelled pigs in a tubular.

In some tubular treating operations, a slug 31 (FIG. 4) of treating chemical (e.g. corrosion inhibitor and/or drag reducer) is passed through tubular 11 "sandwiched" between two spaced gelled pigs 32, 33. To assist in assessing the overall efficiency of this type of operation, it is often desirable to measure the remaining chemical (i.e. the length of the slug 31) as it passes the opposed transducers 12, 13 on tubular.

To measure the length of slug 31, ultrasonic pulses are generated, transmitted, received, and processed in the same manner as described above with the the gated pulses from pulse shaper 29 (FIG. 3A) being fed by line 30a to pulse stretcher 40 (e.g. a retriggerable monostable or one-shot multivibrator) with its delay time set to at least the time interval between ultrasonic pulses. A delay time of two or three pulse intervals is desirable when the signal is noisy.).

Figure 5:
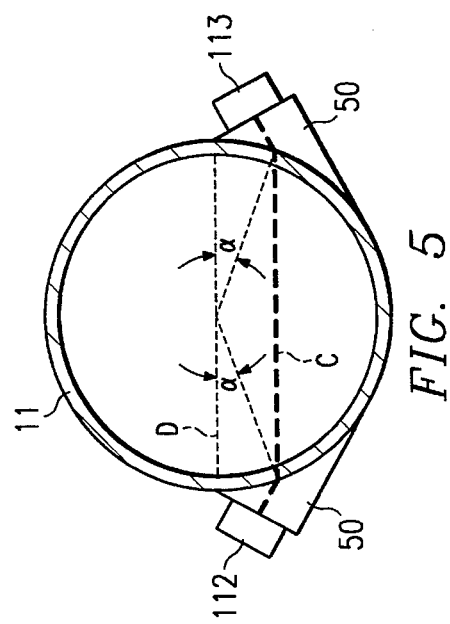
FIG. 5 is a cross-sectional view of still a further embodiment of the apparatus of the present invention.

As the leading pig 32 (FIG. 4) passes transducers 12, 13, a series of gated pulses 32a will be generated (see time curve 29t, FIG. 4) which will be followed by an interval 31a where there are no gated pulses which, in turn is followed by a second series of gated pulses 33a representing the second pig 32. Pulse stretcher 40 processes the series of pulses 32a, 33a to produced two long or "stretched" pulses 32b, 33b, respectively on time curve 40t. The time of interval 31a can then be determined from the number of clock pulses 26 (FIG.3) generated during interval 31a or a timer 41 (FIG. 4) can be used wherein the timer starts as the trailing edge 32E of leading pig 32 passes the transducers and stops when the leading edge 33L of second pig 33 passes the transducers. In either event, the time of interval 31a is then multiplied by the flowrate of the fluids in tubular 11 to arrive at the length of slug 31.

Where a gelled pig has dissolved, eroded, and/or ablated to a point where it no longer fills the entire tubular but, instead, lies below the horizontal diameter "D" (FIG. 5), a further embodiment of the present invention can be used to detect the remaining gelled material as it passes by the transducers 112, 113 on tubular 11. Due to the refraction of the ultrasonic pulses when passed obliquely through the wall of tubular 11, the transducers can not be mounted to transmit or received directly across a chord (e.g. "C") of the tubular. Instead, they must be mounted so that the pulses are originally directed at a refractory angle in relation to the wall of the tubular.

To do this, mounting blocks 50 are used, e.g. a 45°–90°–45° wedge having its hypotenuse cut to the proper curvature to conform with the curvature of the tubular. Both transmitting shear transducer 112 and receiving shear transducer 113 are mounted flush on one leg of a respective wedge so that the pulses generated thereby will enter or exit the wall of tubular 11 at at point approximately 21° (e.g. angle ∝) below diameter D. This will cause the pulses to be refracted to pass through tubular 11 on chord C below the horizontal diameter D to detect gelled material in the lower portion of tubular 11 as it passes therethrough. The placement of the transducers (i.e. ∝=21°) below the horizontal diameter corresponds to about 4.3 inches below the horizontal diameter of a 24-inch diameter tubular. To place the transducers any lower on a tubular will cause the signal strength of the pulses to drop quickly to an unacceptable level.

What is claimed is:

1. A method for detecting and measuring an amount of gelled material as said gelled material passes through a tubular, said method comprising:

generating ultrasonic pulses at timed intervals;

transmitting said pulses through said tubular and materials in said tubular at a fixed point along said tubular;

receiving said pulses after said pulses have passed through said tubular and said materials at said fixed point; and processing said received pulses to determine the number of said received pulses which travelled through said gelled material as said gelled material passed by said fixed point and then processing said number of received pulses to detect and measure the amount of said gelled material.

2. The method of claim 1 wherein said pulses are generated having ultrasonic frequencies.

3. The method of claim 2 wherein said processing of said received pulses includes:

opening a gate to allow said received pulses which travel through said gelled material to pass therethrough while closing the gate to block said received pulses which travel through materials in said tubular other than said gelled material.

4. The method of claim 3 wherein said gate is opened and closed at intervals based on the different velocities at which said pulses travel through said gelled material and said materials other than said gelled materials, respectively.

5. A method of detecting and measuring a slug of chemical which is carried through a tubular between two spaced, pigs comprised of gelled material, said method comprising:

generating ultrasonic pulses at timed intervals;

transmitting said pulses through said tubular and materials in said tubular at a fixed point along said tubular;

receiving said pulses after said pulses have passed through said tubular and said materials at said fixed point; and processing said received pulses to determine the lengths of each of said pigs and the length of the interval therebetween.

6. Apparatus for detecting and measuring an amount of gelled material in a tubular as said gelled material passes by a fixed point along said tubular, said apparatus comprising:

a first transducer for transmitting ultrasonic pulses through said tubular and any materials therein at said fixed point;

a second transducer for receiving said pulses after said received pulses have passed through said tubular and said materials therein;

means for processing said received pulses to identify said received pulses which have passed through said gelled material as said gelled material passes past said fixed point and;

means for processing said identified pulses to detect and measure the amount of said gelled material.

7. The apparatus of claim 6 including:

a clock-driven pulser connected to said first transducer for generating said pulses having ultrasonic frequencies.

8. The apparatus of claim 7 wherein said means for processing said received pulses include:

a gate connected to said receiving transducer adapted to open to allow said received pulses which travel through said gelled material to pass therethrough and close to block said received pulses which travel through the materials in said tubular other than said gelled material.

9. The apparatus of claim 8 wherein said means for processing said received pulses include:

a counter for counting said received pulses which pass through said gate.

* * * * *